United States Patent [19]

Habib

[11] Patent Number: 4,578,065
[45] Date of Patent: Mar. 25, 1986

[54] PROTECTIVE SEALING COMPOSITION IN MOLDED FORM

[75] Inventor: Wagdi W. Habib, Roselle, Ill.

[73] Assignee: Hollister Incorporated, Libertyville, Ill.

[21] Appl. No.: 725,318

[22] Filed: Apr. 19, 1985

Related U.S. Application Data

[63] Continuation-in-part of Ser. No. 272,191, Jun. 10, 1981, Pat. No. 4,534,767, which is a continuation-in-part of Ser. No. 185,003, Sep. 8, 1980, abandoned, which is a continuation-in-part of Ser. No. 90,855, Nov. 2, 1979, abandoned.

[51] Int. Cl.$^4$ ................................................. A61F 5/44
[52] U.S. Cl. ...................................... 604/336; 128/156
[58] Field of Search ................ 604/336; 128/156, 154; 536/114; 252/315.01, 315.6, 315.7, 315.3

[56] References Cited

U.S. PATENT DOCUMENTS

| | | | |
|---|---|---|---|
| 3,302,647 | 2/1967 | Marsan | 604/336 |
| 3,640,741 | 2/1972 | Etes | 252/315.3 |
| 3,954,105 | 5/1976 | Nordby | 128/154 |
| 3,980,084 | 9/1976 | Kross | 604/336 |
| 4,253,460 | 3/1981 | Chen et al. | 604/336 |
| 4,254,008 | 3/1981 | Krsek | 604/336 |

OTHER PUBLICATIONS

Kirk–Othmer, *Encyclopedia of Chemical Technology*, 3rd Ed. vol. 20, Wiley Interscience, New York 1982 pp. 763 and 768.

*Primary Examiner*—C. Fred Rosenbaum
*Assistant Examiner*—Jerome R. Smith, Jr.

[57] ABSTRACT

Protective sealing compositions in the form of molded rings or sheets, which comprise gelled mixtures of water-absorbing particulate hydrocolloid gum and non-toxic liquid polyhydroxy alcohol are provided with increased resistance to the drained fluid (viz. urine or intestinal fluids) by incorporating a small amount of fumed silica or colloidal silica gel. By controlling the amount of silica added appreciable reductions in the wet tack and/or dry tack of the composition can be avoided. The compositions can be used with ostomy, wound drainage and incontinence devices.

8 Claims, No Drawings

PROTECTIVE SEALING COMPOSITION IN MOLDED FORM

RELATED APPLICATIONS

This application is a continuation-in-part of co-pending application Ser. No. 272,191, filed June 10, 1981, now U.S. Pat. No. 4,534,767, being a continuation-in-part of application Ser. No. 185,003, filed Sept. 8, 1980 (now abandoned), which was a continuation-in-part of application No. 90,855 filed Nov. 2, 1979 (now abandoned).

FIELD OF INVENTION, BACKGROUND AND PRIOR ART

The field of the invention is moldable sealing compositions for application to the skin around surgical or natural drainage openings in the body, such as for use with ostomy, wound drainage, and incontinence devices. More particularly, the invention concerns an improvement in karaya-glycerin type sealing compositions.

Protective sealing compositions in the form of molded rings or sheets for application around surgical fluid drainage openings are in common use. A well-known formulation for such compositions comprises a gelled mixture of karaya gum and glycerin. (See, for example, U.S. Pat. Nos. 3,302,647 and 3,954,105.) Where the drainage opening is a stoma, the karaya-glycerin sealing composition may be used in the form of a molded ring which is placed around the stoma between the gasket of the ostomy appliance and the body of the wearer. The purpose of the ring is to provide a protective seal. It is desired to prevent the intestinal fluid or urine being discharged from the stoma from leaking around the ring, all the discharged fluid being collected in the bag or pouch of the ostomy appliance. The sealing ring also performs the function of protecting the skin area around the stoma from the irritating urine or intestinal fluid, which in the case of ileostomies may include gastric juices. Karaya-glycerin sealing compositions may also be used in the form of a sheet or blanket. Such blankets may also be used around stoma openings, or they may be used around drainage openings associated with a wound or surgical incision.

Sealing compositions of the kind described preferably have an initial tackiness, usually referred to as "dry tack," so that they will provide an initial adhesive adherence to the skin around the drainage opening. It is particularly important that the compositions provide a high degree of adhesiveness while in contact with aqueous fluid. This is usually referred to as "wet tack." The hydrocolloid in the composition, such as karaya, absorbs water which causes the hydrocolloid to swell and to increase in tackiness. However, with continued exposure to the aqueous fluid, especially where the fluid is urine or an intestinal discharge containing gastric juices, the composition tends to break down, losing mechanical strength, and eventually becomes ineffective for its desired protective sealing function. In application, such sealing rings or blankets must be frequently replaced. It has been desired to increase the mechanical and/or adhesive endurance of such rings or blankets formed from a karaya-glycerine composition, but heretofore no satisfactory means has been provided for accomplishing this result.

SUMMARY OF INVENTION

The present invention is based in part on the discovery that a new and surprising result is obtained by the incorporation of a small amount of certain types of colloidal silica in protective sealing compositions, which are composed of a mixture of hydrocolloid gum and polyhydroxy alcohol. More specifically, the resistance of such compositions in the form of molded rings or sheets to degradation by intestinal fluids and/or urine can be markedly increased. By controlling the amount of silica dispersed in the composition, the mechanical endurance of the composition can be increased without appreciably reducing its wet tack, and a satisfactory dry tack may also be obtained.

DETAILED DESCRIPTION

The present invention is applicable to protective sealing compositions prepared from gelled mixtures of a particulate hydrocolloid gum and a liquid polyhydroxy alcohol, which are capable of being formed into molded rings or sheets and set by gelation. Based on present usage, the hydrocolloid gum is preferably karaya gum, but other gellable hydrocolloid gums can be used as a partial or complete substitute for the karaya. Such gellable hydrocolloid gums include ghatti, zedou, tragacanth, gelatin, dextran, pectin, xanthane, and similar natural gums. Synthetic gums may be used, including sodium carboxymethylcellulose and hydroxyethyl cellulose. Such hydrocolloid gums are characterized by being poly-saccharides, by being hydrophilic and water-absorbing, and by being gellable in admixture with glycerin or other polyhydroxy alcohol.

For the purpose of the present invention, the hydrocolloid gums are used in a fine particulate form (viz. as powders). Karaya gum, for example, is usually employed in a sufficiently fine state of subdivision that the powder will pass a 100 mesh or finer screen. The powdered gums as used are air-dry, that is, dry to the touch, but may contain some moisture, such as 10 to 18% by weight moisture.

The principal liquid component of the sealing composition is preferably a non-toxic liquid polyhydroxy alcohol. Based on present usage, glycerin is the preferred alcohol, but other polyhydroxy alcohols of similar properties can be used, such as, for example, propylene glycol, sorbitol, etc. Preferably, the polyhydroxy alcohol is not only non-toxic and non-irritating when applied to the skin, but, in addition, has a soothing or emollient action as provided by glycerin or similar emollient polyhydroxy alcohols.

In preparing the sealing composition, a sufficient amount of the polyhydroxy alcohol is employed to form a flowable mix, which can be formed or molded into the desired ring or sheet shape, and then set by gelation. The relative proportions of the polyhydroxy alcohol and the hydrocolloid can be varied while still achieving these general results. If too small an amount of the alcohol is present, the mix will be too stiff for flowing into the mold, while if too much of the alcohol is present, the molded composition will be too soft and insufficiently gelled. In accordance with present practice in relation to mixes of karaya gum and glycerin, approximately equal parts by weight of the gum and the alcohol give good results. However, a moldable mix can be prepared using more or less of the glycerin or other polyhydroxy alcohol. In general, the mix may contain from 35 to 55% of the karaya or other hydrocolloid, and from 35 to 55% of glycerin or other polyhydroxy alcohol. As a more specific example, mixes can be prepared using portions within the range from 80 to 120 parts by weight of glycerin per 100 parts of karaya gum.

In accordance with the present invention, certain kinds of colloidal silica are incorporated in the sealing composition, the silica preferably being homogeneously dispersed therein. Fumed silica is preferred, although colloidal silica gel can also be used. Fumed silica is produced by flame hydrolysis of silicon tetrachloride. It can be obtained from various manufacturers, including the "Cab-O-Sil" products of Cabot Corporation, Boston, Mass., and the "Aerosil" products of Degussa, Inc., New York, N.Y., U.S.A. These products are silicon dioxide in colloidal form having very high surface areas, for example, one suitable specific product is the Grade M-5 of Cab-O-Sil.

Colloidal silica gel is prepared from precipitated amorphous silica gel. It consists of fine particles of high surface area. Colloidal silica gels can be obtained from the Davison Chemical Division of W. R. Grace & Co., Baltimore, Md., being sold under the trademark "Syloid." One suitable product is Syloid 244.

In the broadest aspect of this invention, the colloidal silica (fumed silica or colloidal silica gel) is incorporated in the composition in an amount of from 0.1 to 4.0% by weight. (This and other stated percentages are based on the total weight of the composition, including the silica and all other ingredients of the finished product.) Within the stated range the endurance of the gel composition in contact with urine and/or intestinal fluids is markedly increased while the wet tack adhesive property remains adequate. However, it is preferable not to use over 1.5% silica (viz. from 0.1 to 1.5%) so that the dry tack and wet tack properties are more fully retained.

To reduce the viscosity of the mix, and to facilitate its molding or forming, it has been found desirable to incorporate sodium carboxymethylcellulose (CMC) in the mix. For example, from 2 to 15% of CMC may be used. In representative formulations, from 3 to 8 parts by weight of CMC is combined with 40 to 50 parts each of karaya and glycerin, and from 0.5 to 1.2 parts of fumed silica. Where the CMC is omitted, the optimum amount of the fumed silica is somewhat lower, such as from 0.2 to 0.8% of the mix.

The compositions may include other minor ingredients, such as preservatives or antibacterial agents. For example, an alkyl para-hydroxy benzoate or a mixture of such benzoates may be used as the preservative. For example, a mixture of methyl, ethyl, propyl, and butyl parabens can be used. Where parabens are employed, such as in amounts from 0.1 to 0.5%, it may be desirable to first dissolve the parabens in propylene glycol or other co-solvent with glycerin, in which the parabens are more soluble than in glycerin. For example, from 2 to 10 parts of propylene glycol can be used per 100 parts of glycerin.

In combining the ingredients to prepare the fluid molding composition, the parabens may first be dissolved in the small amount of propylene glycol, and then the propylene glycol solution of the paraben mixed with the larger amount of glycerin. The fumed silica can then be dispersed in the combined polyhydroxy alcohols by mixing until a uniform dispersion is obtained. The hydrocolloid gum powder is next added, and the mixing is continued until the composition is uniformly mixed. The composition is then molded prior to gellation, which may occur within 5 to 10 minutes. For molding, the composition can be poured into ring or sheet mold forms, and formed under light pressure to the desired shape, such as by use of a movable mold die or platen as the upper mold member. During the molding process, the composition will set up rapidly to a gel state. Where desired, gelation can be promoted by heating the composition, either in the mold, or subsequent to molding. For example, microwave heating may be applied to the composition in the mold, or the formed rings or sheets may be passed through an infrared heating tunnel. The temperature of heating is not highly critical, since gelation will occur and become completed at room temperature. However, by heating the molded sheets or rings to a temperature of about 160° to 180° F., completion of the setting and gelation occurs in a shorter time. During the setting, there is ordinarily no loss of the polyhydroxy alcohol, and therefore the composition should not be heated to a temperature above the boiling point of the polyhydroxy alcohol.

The practice of the present invention in preferred embodiments and the results obtained thereby are further illustrated by the following examples.

EXAMPLE I

In a presently preferred embodiment, a protective sealing composition is prepared in accordance with the present invention using the following formula.

| FORMULA A | |
|---|---|
| Ingredients | Weight % |
| (1) 2% colloidal silica[a] in glycerin blend[d] | 50.0 |
| (2) Karaya gum powder[b] | 45.0 |
| (3) Sodium Carboxymethylcellulose (CMC)[c] | 5.0 |
| | 100.0 |

[a]Provides 1% colloidal silica; fumed silica Cab-O-Sil M-5 (Cabot Corporation, Boston, Massachusetts), or colloidal silica gel, Syloid 244 (Davison Chemical Division, W. R. Grace & Co., Baltimore, MD).
[b]Smaller than 140 mesh; 10 to 18% moisture.
[c]CMC 7HOX8F (Hercules, Incorporated, Wilmington, Delaware).
[d]Glycerin Blend: 94.795% glycerin, 4.839% propylene glycol, 0.161% methylparaben, 0.028% propylparaben, and 0.177% butylparaben.

In compounding the above ingredients, the glycerin blend with the fumed silica uniformly dispersed therein is mixed with the karaya gum powder and the sodium carboxymethylcellulose until a uniform gellable mixture is obtained. This mixture, prior to gelation, is poured into molds for forming rings or sheets, and is cured in the molds to produce the ring or sheet product. The curing may be obtained by leaving the composition in the molds overnight at ambient room temperature. Alternatively, the curing may be accelerated by applying heat from infrared lights or by microwave radiation. Microwave heating is preferred.

To improve dry tack, if desired, a small amount of a suitable pressure sensitive adhesive is deposited in the bottoms of the molds before filling them with the mix. For example, the adhesive may be the "H49" vinyl acrylic medical pressure-sensitive adhesive of U.S. Adhesives, Chicago, Ill., U.S.A.

EXAMPLE II

In another embodiment, a protective sealing composition is prepared in accordance with the present invention using the following formula.

FORMULA B

| Ingredients | Weight % |
| --- | --- |
| (1) Propylene glycol (USP) | 2.250 |
| (2) Methylparaben | 0.075 |
| (3) Propylparaben | 0.013 |
| (4) Butylparaben | 0.082 |
| (5) Glycerin (USP, 99%) | 46.580 |
| (6) Colloidal silica (see note "a" Ex. 1) | 0.500 |
| (7) Karaya gum powder (10–18% moisture, −140 mesh) | 50.500 |
| | 100.000 |

In compounding the above ingredients, ingredients (2) to (4), the parabens, are dissolved in ingredient (1), the propylene glycol. This solution is added to ingredient (5), the glycerin, and mixed until uniform. Ingredient (6), the silica, is then dispersed in the liquid solution of the preceding ingredients, and the dispersion is mixed until uniform. The karaya powder, ingredient (7), is then added with mixing continued until a uniform gelable mixture is obtained. This mixture, prior to gelation, is poured into molds for forming rings or sheets, and is cured in the molds to produce the ring or sheet product. The curing may be obtained by leaving the composition in the molds overnight at ambient room temperature. Alternatively, the curing may be accelerated by applying heat from infrared lights or by microwave radiation.

EXAMPLE III

A composition is prepared as described in Example II except that algin powder is substituted on an equal weight basis for the karaya gum powder. The algin is supplied by Kelco Company, Clark, N.J.

EXAMPLE IV

Using the compounding procedure described in Example II, a protective sealing composition is prepared according to the following formula.

FORMULA C

| Ingredients | Weight % |
| --- | --- |
| (1) Propylene glycol (USP) | 2.880 |
| (2) Methylparaben | 0.098 |
| (3) Propylparaben | 0.017 |
| (4) Butylparaben | 0.105 |
| (5) Glycerin (USP, 99%) | 56.400 |
| (6) Fumed silica or colloidal silica gel | 0.500 |
| (7) Xanthan gum | 40.000 |
| | 100.000 |

In the foregoing formula, the xanthan gum is a food grade product supplied by Kelco Company, Clark, N.J.

EXAMPLE V

A protective sealing composition is prepared using the compounding and molding procedure of Example II, as applied to the following formula.

FORMULA D

| Ingredients | Weight % |
| --- | --- |
| (1) Propylene glycol (USP) | 2.370 |
| (2) Methylparaben | 0.079 |
| (3) Propylparaben | 0.014 |
| (4) Butylparaben | 0.087 |
| (5) Glycerin (USP, 99%) | 46.450 |
| (5A) Sorbitol (USP, 70%) | 5.000 |
| (6) Fumed silica or colloidal silica gel | 1.500 |
| (7) Gum zedou powder | 44.500 |
| | 100.000 |

In mixing the foregoing ingredients, ingredients (5) and (5A), the glycerin and sorbitol, are combined as described for the glycerin, ingredient (5), in the procedure of Example I.

EXAMPLE VI

A protective sealing composition is prepared according to the compounding procedure of Example II using the formula set out below.

FORMULA E

| Ingredients | Weight % |
| --- | --- |
| (1) Propylene glycol (USP) | 3.05 |
| (2) Methylparaben | 0.10 |
| (3) Propylparaben | 0.02 |
| (4) Butylparaben | 0.11 |
| (5) Glycerin (USP, 99%) | 59.72 |
| (6) Fumed silica or colloidal silica gel | 2.00 |
| (7) Sodium Carboxymethylcellulose | 35.00 |
| | 100.000 |

The sodium carboxymethylcellulose is CMC 7HOXF, supplied by Hercules, Incorporated, Wilmington, Del. The molded rings or sheets are preferably cured by microwave heating.

EXAMPLE VII

A protective sealing composition was prepared according to the following formula.

FORMULA F

| Ingredients | Weight % |
| --- | --- |
| (1) Propylene glycol (USP) | 2.710 |
| (2) Methylparaben | 0.090 |
| (3) Propylparaben | 0.020 |
| (4) Butylparaben | 0.100 |
| (5) Glycerin (USP, 99%) | 53.080 |
| (6) Deionized water | 3.000 |
| (7) Fumed silica or colloidal silica gel | 1.000 |
| (8) Sodium carboxymethylcellulose | 15.000 |
| (9) Gum karaya powder | 25.000 |
| | 100.000 |

In compounding the above ingredients, the same mixing procedure is used as described in Example II with reference to ingredients (1) to (5). Ingredient (6), the deionized water, is then added, and the mixing is continued to produce a uniform mixture. Ingredient (7), the fumed silica, is then dispersed in the liquid solution to form a uniform dispersion. Ingredient (8), the sodium carboxymethylcellulose, is then added with continued mixing, and ingredient (9), the karaya, is added last, and the mixing continued until a uniform gelable composition is obtained. The molding and gelling procedure is the same as described in Example II.

EXAMPLE VIII

A comparative endurance test using a formula as set out below with and without colloidal silica gel at the level of 1%.

| COMPARATIVE FORMULA | | |
|---|---|---|
| Ingredients | Without Colloidal Silica (wt. %) | With Colloidal Silica (wt. %) |
| Karaya Powder | 46% | 45% |
| CMC | 5 | 5 |
| Colloidal silica gel | 0 | 1 |
| Glycerin | 46.4001 | 46.4001 |
| Propylene Glycol | 2.4201 | 2.4201 |
| Methylparaben | .0789 | .0789 |
| Propylparaben | .0142 | .0142 |
| Butylparaben | .0867 | .0867 |

In the above formula, the CMC was sodium carboxymethylcellulose, and the colloidal silica gel was Syloid 244 (Davison Chemical Division, W. R. Grace & Co.)

The results of the test are summarized in the following table.

| | Endurance Time (hours/gram) |
|---|---|
| Without colloidal silica | 2.7 hours[1] |
| With colloidal silica | 15.2 hours[1] |

[1] Averages of six trials.

As shown by the above data, the endurance of the karaya-glycerin composition exposed to simulated urine was increased by over 500%. Colloidal silica gel is believed to be the best available alternative to fumed silica for increasing the endurance of a karaya-glycerin composition in contact with degradative bodily fluids.

For the endurance tests, the simulated urine was prepared as described in Remington's *Pharmaceutical Sciences*, "Urine," pp. 598–9, Ed 15 (1975). The endurance test apparatus includes a tank for containing the simulated urine, and a plurality of tripod testing fixtures, which may be placed in the tank in contact with the solution. The testing fixture has a platform at the top with a sample-receiving recess. The center portion of the recess is cut out to provide an opening through the platform. When placed in test position, the test samples bridge the openings. U-shaped weights are then placed over the samples. These weights are in the form of steel hooks weighing approximately 7.4 grams. In use, the hooks are placed over the samples so that when the hooks break through the samples they would fall freely through the openings in the platforms. Nylon strings are attached to the upper cross-arm portions of the inverted U-shaped hooks and the strings are attached to the operating levers of micro switches, the lengths of strings being selected so that when the sample is broken, the micro switch will be activated, and a timing clock for the particular sample will be stopped. In starting the test, after the samples have been placed in the tank and the strings attached to the microswitch levers, the simulated urine or intestinal fluid is added to the tanks to a level above the position of the samples, and the timing clocks for each sample are started. The elapsed time for breakthrough of each sample is thereby automatically recorded.

The samples for the endurance tests were cut sections of rings molded from the comparative formulas. Each test sample has a weight of approximately 1.0 grams, and had an elongated shape. The center portions of the samples engaged by the weighted hooks had dimensions of approximately 0.15 by 0.3 inches. The measured time for breakthrough was corrected by multiplying the measured time by 1.0 grams of the sample divided by actual weight of the sample.

I claim:

1. A protective sealing composition in the form of a molded gelled ring, sheet, or the like, said composition comprising essentially a gelled mixture of gelable, water-absorbing, particulate hydrocolloid gum and a non-toxic liquid polyhydroxy alcohol, wherein the improvement comprises having dispersed in said composition an amount of colloidal silica gel within the range from 0.1 to 4.0% by weight, said amount of colloidal silica gel being effective to increase appreciably the mechanical endurance of said sealing composition when exposed to urine.

2. The composition of claim 1 in which said colloidal silica gel is present in an amount from 0.1 to 1.5% by weight.

3. A protective sealing composition in the form of a molded gelled ring, sheet, or the like, said composition comprising essentially a gelled mixture of karaya gum powder and a non-toxic liquid polyhydroxy alcohol, wherein the improvement comprises having dispersed in said composition an amount of colloidal silica gel within the range from 0.1 to 4.0% by weight, said amount of colloidal silica gel being effective to increase appreciably the mechanical endurance of said sealing composition, when exposed to urine.

4. The composition of claim 3 in which said colloidal silica gel is present in an amount from 0.1 to 1.5% by weight.

5. The composition of claim 3 in which said alcohol is selected from the group consisting of glycerin and mixtures of glycerin and propylene glycol.

6. The composition of claim 4 in which said alcohol is selected from the group consisting of glycerin, and mixtures of glycerin and propylene glycol.

7. The composition of claim 6 wherein the improvement further comprises having from 2 to 15% by weight of sodium carboxymethylcellulose in said composition.

8. A protective sealing composition in the form of a molded gelled ring, sheet, or the like, said composition being composed essentially of a gelled mixture of karaya gum powder and glycerin, wherein the improvement comprises having dispersed in said composition an amount of from 0.1 to 1.5% by weight of colloidal silica gel together with 3 to 8% by weight of sodium carboxymethylcellulose, said amount of colloidal silica gel being effective to increase appreciably the mechanical endurance of said sealing composition when exposed to urine.

* * * * *